(12) United States Patent
Kobayashi et al.

(10) Patent No.: US 7,919,080 B2
(45) Date of Patent: Apr. 5, 2011

(54) IMMORTALIZED HEPATOCYTE CELL LINE SECRETING MODIFIED INSULIN WITH GLUCOSE SENSITIVITY

(76) Inventors: Naoya Kobayashi, Okayama (JP); Noriaki Tanaka, Okayama (JP); Teru Okitsu, Okayama (JP); Ji-Won Yoon, Alberta (CA); Hee-Sook Jun, Alberta (CA); Seungjin Shin, Alberta (CA)

( * ) Notice: Subject to any disclaimer, the term of this patent is extended or adjusted under 35 U.S.C. 154(b) by 537 days.

(21) Appl. No.: 11/984,006

(22) Filed: Nov. 13, 2007

(65) Prior Publication Data

US 2009/0209033 A1     Aug. 20, 2009

Related U.S. Application Data

(62) Division of application No. 10/432,592, filed as application No. PCT/JP02/10244 on Oct. 2, 2002, now Pat. No. 7,312,077.

(51) Int. Cl.
*A01N 63/00* (2006.01)
*A01N 65/00* (2006.01)
*A61K 48/00* (2006.01)

(52) U.S. Cl. ................................. 424/93.21; 424/93.2

(58) Field of Classification Search .................. None
See application file for complete search history.

(56) References Cited

U.S. PATENT DOCUMENTS 6,194,176 B1   2/2001   Newgard et al.
7,033,744 B2   4/2006   Kobayashi et al. ............ 435/1.1

FOREIGN PATENT DOCUMENTS

WO   WO 99/35245 A2   7/1999
WO   WO 00/04171      1/2000
WO   WO 00/18239 A    4/2000

OTHER PUBLICATIONS

Thule, et al. (2000) Gene Therapy, 7: 205-214.*
Tuch, et al. (2003) Gene Therapy, 10: 490-503.*
Zhang, et al. (1996) Nucleic Acids Research, 24(4): 543-48.*
Totsugaya, T. et al., Establishment of hTERT-immortalized human hepatocytes as a source for a hybrid bioartificial liver., Hepatology, 2001, vol. 34, No. 4, Pt.2, pp. 305A, 531.
Lee, H.C. et al., Remission in models ofo type 1 diabetes by gene therapy using a single-chain insulin analogue., nature, 2000, vol. 408, No. 23, p. 483-8.
Cai, J. et al., Construction of a non-tumorigenic rat hepatocyte cell line for transplantation: reversal of hepatocyte immortalization by site-specific excision of the SV40 T antigen., J Hepatol, 2000, vol. 33, No. 5, p. 701-8.
Davies, E. L. et al, Glucose-sensitive insulin-secreting AtT20 cells: A model for insulin delivery by somatic cell gene therapy, Diabetologia, 1996, vol. 39, suppl.1, p. A137, 518.

* cited by examiner

*Primary Examiner* — Robert M Kelly
(74) *Attorney, Agent, or Firm* — Kratz, Quintos & Hanson, LLP

(57) ABSTRACT

The present invention provides a cell line which can be substituted for β cells in human mature pancreatic islets and express insulin in a glucose-concentration dependent manner, and enables the easy obtainment of the number of cells which meets the demand. The present invention also provides a therapeutical cell preparation for treating diabetes. The cell lines of the present invention can be obtained by integrating both a nucleotide sequence encoding tamoxifen-induced Cre recombinase and a nucleotide sequence encoding insulin regulated by glucose-sensitive promoter into the chromosome in a human immortalized hepatic cell line FERM BP-7498 containing the TERT gene inserted in between a pair of LoxP sequences.

4 Claims, 4 Drawing Sheets

LPK 28S rRNA

SEQUENCE LISTING

```
<160> NUMBER OF SEQ ID NOS: 3

<210> SEQ ID NO 1
<211> LENGTH: 34
<212> TYPE: DNA
<213> ORGANISM: P1 pharge
<220> FEATURE:
<223> OTHER INFORMATION: LoxP sequence

<400> SEQUENCE: 1
ataacttcgt atagcataca ttatacgaag ttat                              34

<210> SEQ ID NO 2
<211> LENGTH: 7
<212> TYPE: PRT
<213> ORGANISM: Artificial Sequence
<220> FEATURE:
<223> OTHER INFORMATION: Description of Artificial Sequence: linker
      sequence
```

```
<400> SEQUENCE: 2

Gly Gly Gly Pro Gly Lys Arg
1               5

<210> SEQ ID NO 3
<211> LENGTH: 183
<212> TYPE: DNA
<213> ORGANISM: Artificial Sequence
<220> FEATURE:
<223> OTHER INFORMATION: Description of Artificial Sequence:
      recombinant DNA sequence encoding a single-chain insulin
      analogue

<400> SEQUENCE: 3
atgttcgtta atcagcacct gtgcggctct cacctggtag aagctctgta cctggtttgc        60
ggtgaacgtg gtttttctca caccccgaaa accggtggtg gtccgggtaa acgtggcatc       120
gttgaacaat gctgtactag catctgctct ctctaccagc tggagaacta ttgtaactag       180
taa                                                                     183
```

IMMORTALIZED HEPATOCYTE CELL LINE SECRETING MODIFIED INSULIN WITH GLUCOSE SENSITIVITY

CROSS REFERENCE TO RELATED APPLICATION

This application is a division of Ser. No. 10/432,592, filed Jun. 2, 2003, now U.S. Pat. No. 7,312,077, issued Dec. 25, 2007, which is a 35 U.S.C. 371 application of international application No. PCT/JP02/10244 filed Oct. 2, 2002.

DEPOSIT

Human immortalized hepatocyte cell line secreting insulin with glucose sensitivity has been give Accession number FERM BP-7498 by the International Deposit Authority (IDA). FERM BP-7498 was received by the IDA on Mar. 7, 2001. The IDA is the International Patent Organism Depositary, National Institute of Advanced Industrial Science and Technology located at AIST Tsukuba Central 6, 1-3, Higashi 1-Chome, Tsukuba-shi, Ibaraki-ken 305-8566 Japan.

TECHNICAL FIELD

The present invention relates to a cell line secreting insulin with glucose sensitivity. In particular, the present invention relates to a hepatocyte cell line secreting insulin with glucose sensitivity, which can reversibly proliferate. In addition, the present invention relates to a therapeutical cell preparation used in medical treatment for diabetes.

BACKGROUND ART

In 2000, seven cases of clinical islet transplantation were reported from University of Alberta in Edmonton, Canada (Shapiro A M, Lakey J R, Ryan E A, et al., N Engl J Med 343:230-238, 2000). The report was that by a novel method for using immunosuppressant which was called "Edmonton Protocol" later, all the cases with type I diabetes who underwent pancreatic islet transplantation became free from daily administration of insulin. At the present time, pancreatic islet transplantation is the closest to an ideal curing method for patients with insulin-dependent diabetes mellitus.

Pancreas under retroperitoneum is composed of exocrine gland and endocrine glands. Exocrine gland accounts for at least 98% of the whole pancreas volume, whereas endocrine glands account for at most 2%. Endocrine tissue which was found by Langerhans in 1869 is called pancreatic islet. Pancreatic islet is an aggregate of endocrine cells, and comprises α cells, β cells, PP cells and δ cells and the like. Insulin is secreted by β cells in pancreatic islets, said insulin being the only endogenous hormone which has the effect of decreasing blood sugar. The aim of pancreatic islet transplantation is to replace a system for decreasing blood sugar, said system which has declined, and regenerate one by separating pancreatic islets from pancreas and transplanting them to a patient who suffers from insulin-dependent diabetes mellitus.

Whether or not pancreatic islets are successfully separated depends on the quality of pancreas itself used for the separation. In addition, in order to successfully separate pancreatic islets, it is necessary that exocrine gland tissue should be in a good condition. Tact beyond expectation is required in the case where pancreas is taken for the purpose of separating pancreatic islets. If pressure is only applied to pancreas by touching the pancreas, for example, the pancreatic exocrine cells release proteases which these cells contain, followed by autocytolysis. In the case pancreas is separated at a distant place, it is necessary that the pancreas should be preserved with great caution during the transport of it to facilities for the separation of the cells.

Based on the cause of decline in insulin activity, diabetes is generally classified into type I diabetes juvenile-onset diabetes) and type II diabetes. Because the control of blood sugar by insulin treatment is extremely difficult in the case of type I diabetes in which insulin is little secreted compared with the case of type II diabetes in which the secretion of insulin is maintained within a certain extent, pancreatic islet transplantation is considered as the most effective treatment. Also in type II diabetes, insulin shortage is caused by glucose toxicity or β-cell fatigue if the stage progresses. However, pancreatic islet transplantation has not been indicated for type II diabetes. The reason is that there is insulin resistance in a basic condition of type II diabetes, whereby it is worried whether or pancreatic islet transplantation is effective. Although the exact control of blood sugar leads a good convalescence in type II diabetes, the case of type I diabetes alone is the subject of pancreatic islet transplantation on the basis of the real fact that pancreatic islets for transplantation is in short supply. In the future if comes the situation where a great number of pancreatic islets for transplantation can be supplied, there is a great possibility that pancreatic islet transplantation is indicated for insulin dependent diabetes mellitus with insulin resistance.

At the time when insulin treatment was developed, it was believed that type I diabetes became a completely controllable disease by insulin treatment. However, it was found that insulin treatment caused a long-term complication such as retinopathy, neuropathy or nephropathy, and that type I diabetes brought patients other suffering in the form of a chronic disease. Insulin treatment plays a key role in solving the emergency problem of a prompt death in type I diabetes, and in the point that insulin treatment can be offered to any patient at the present time. However, insulin treatment can not be a method for treating type I diabetes completely, an extremely difficult problem such as the risk of hypoglycemia or long-term complications persists.

Type I diabetes is caused by autoimmune abnormalities in which pancreatic β cells secreting insulin are specifically destroyed (Atkinson M A, Maclaren N K., N Engl J Med 331:1428-1436, 1994). To completely treat type I diabetes, transplantation which is one of the treatments for regenerating and substituting for pancreatic β cells is considered. As a transplantation, there are a pancreas transplantation and a pancreatic islet transplantation. The purposes of these two kinds of transplantation is to enable the extremely exact control of blood sugar, and to prevent hypoglycemia and a long-term complication from being caused. It is not the only purpose to release patients from daily bother in insulin treatment and then improve the quality of life (QOL). As a measure to achieve the goal of completely curing insulin-dependent diabetes mellitus, transplantation therapies have much greater possibilities than insulin treatment does. In pancreas transplantation, however, there are problems that an operative risk is serious, and that the complications caused by a concomitantly transplanted exocrine gland can be severe. In the case of pancreatic islet transplantation, there is a problem of safety caused by using immunosuppressant. Another problem is that much smaller is the number of pancreases taken from neomorts necessary for the separation of pancreas/pancreatic islets, compared with the number of patients in need thereof, and consequently there is no probability that the situation will be overcome.

As a source of cells which substitute for human mature pancreatic β cells, human ES cells and tissue stem cells, for example, are being intensively studied at the present time. Although it was reported that insulin expression was observed after induction of differentiation in the case of some kinds of cells (murine ES cells and hepatic stem cells), it is still unclear which gene(s) should be introduced at which stage for effective insulin secretion. In addition, the use of such stem cells essentially involves difficulties in control, said difficulties arising from the fact that these stem cells have pluripotency and active proliferation potency. It is considered that plenty of time is necessary to put these cells to practical use in the future.

Study using porcine tissues/cells progresses, whereas these problems of xenozoonosis, tissue compatibility and ethics have surfaced. In special, potential risks connected with virus have become a big problem. Risks that virus which porcine organs or cells contain infects a recipient thereby causing a disease (it is especially impossible to remove porcine endogenous retrovirus (PERV), because PERV is integrated in chromosome) include the risk, for example, that the infection spreads to the family and medical staff, and consequently new virus infection spreads in the world.

At the present time, therefore, deeply desired is a source of cells which is preferable in quality and amount (quantity), and substitutes for human mature pancreatic β cells.

An object of the present invention is to solve conventional problems, and to provide a cell line which can express insulin in a glucose-concentration dependent manner, and enables the easy obtainment of the number of cells, said number which meets the demand. Another object is to provide a therapeutical cell preparation for diabetes treatment.

DISCLOSURE OF INVENTION

As a result of an intensive study to solve the above problems, the present inventors have found that when Cre recombinase expression vector is introduced to a reversibly-proliferating hepatic cell line FERM BP-7498 which was established by the present inventors, obtained is a cell line which maintains properties to produce L-type pyruvate kinase (LPK) in a glucose-concentration dependent manner. It was found, on the basis of the fact, that when an insulin-gene expression vector controlled by LPK promoter was introduced to the cell line, the resulting cells could produce insulin in a glucose-concentration dependent manner and they were used as an effective therapeutical cell preparation for diabetes, whereby the present invention has been completed.

Thus, the present invention relates to an immortalized hepatic cell line secreting insulin with glucose sensitivity, said cell line being obtained by integrating both a nucleotide sequence encoding tamoxifen-induced Cre recombinase and a nucleotide sequence encoding insulin under the control of glucose-sensitive promoter into the chromosome in a human immortalized hepatic cell line FERM BP-7498, said chromosome having a human telomerase reverse transcriptase gene (hereinafter referred to as "hTERT gene"), said hTERT gene being inserted in between a pair of LoxP sequences.

The present invention also relates to an immortalized hepatic cell line secreting insulin with glucose sensitivity, FERM BP-8127.

The present invention relates to a hepatic cell line secreting insulin with glucose sensitivity, said cell line being obtained by removing the hTERT gene inserted in between a pair of LoxP sequences from the immortalized hepatic cell line secreting insulin with glucose sensitivity.

In addition, the present invention relates to a medicine for treating diabetes, which comprises cells obtained by removing the hTERT gene inserted in between a pair of LoxP sequences from the immortalized hepatic cell line secreting insulin with glucose sensitivity.

BRIEF DESCRIPTION OF DRAWINGS

In FIG. 2, numeral 3 denotes cytoplasm and numeral 4 denotes a cell nucleus.

BEST MODE FOR CARRYING OUT THE INVENTION

Figure 1:
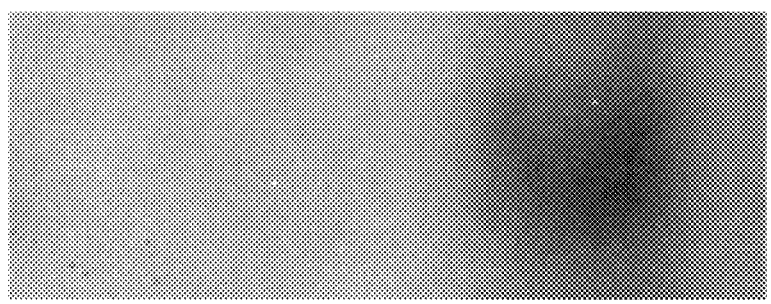
FIG. 1 is a figure showing a result of northern blotting.
Figure 1:
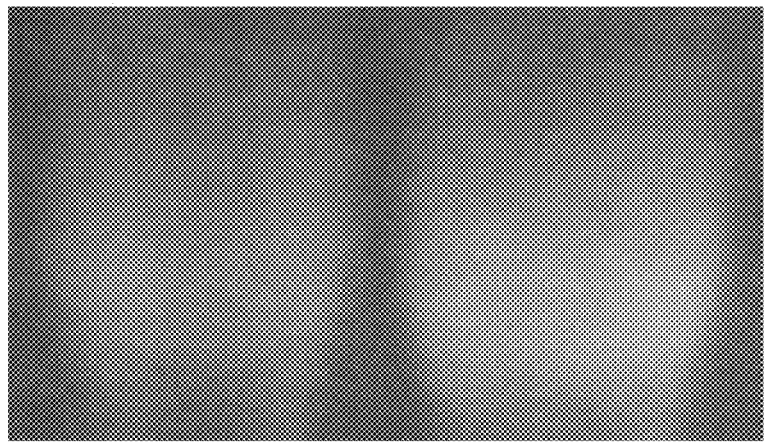

An immortalized hepatic cell line secreting insulin with glucose sensitivity and a medicine for treating diabetes of the present invention are explained as follows, said medicine comprising cells obtained by removing the hTERT gene inserted in between a pair of Lox P sequences from the immortalized hepatic cell line secreting insulin with glucose sensitivity.

The immortalized hepatic cell line secreting insulin with glucose sensitivity of the present invention (hereinafter referred to as "immortalized insulin-secreting hepatic cells") is a cell line obtained by integrating both a nucleotide sequence encoding tamoxifen-induced Cre recombinase and a nucleotide sequence encoding insulin regulated by glucose-sensitive promoter into the chromosome in a human immortalized hepatic cell line FERM BP-7498, said chromosome having the hTERT gene which has been inserted in between a pair of LoxP sequences.

The human immortalized hepatic cell line FERM BP-7498 is a hepatic cell line immortalized by introducing a normal hTERT gene inserted in between a pair of LoxP sequences into the chromosome in human hepatic cells. The cell line FERM BP-7498 is not tumorigenic, and shape thereof is close to that of a normal hepatic cell. The cell line FERM BP-7498 rather maintains liver-specific functions and proliferates in a short term with no need of any special culture condition. In addition, the cell line FERM BP-7498, as well as normal cells, maintains the properties to take in glucose in blood in response to the blood sugar level, and the properties to produce L-type pyruvate kinase (LPK) in a glucose-concentration dependent manner.

The above-mentioned LoxP sequence is a known site-specific recombinant sequence which is recognized by Cre recombinase. In between the sequences, performed is homologous recombination comprising the steps of excising, exchanging and coupling DNA-strands. The LoxP sequence comprises 34 bases of "ATAACTTCGTATAGCATACATTATACGAAGTTAT" (SEQ ID NO: 1). When a pair of LoxP sequences inserted in the same direction is located in a DNA molecule, the DNA sequence flanked by the sequences is excised to become a circular molecule (excision reaction).

The above-mentioned hTERT gene is originated from TERT gene in a normal cell. hTERT gene is a gene whose expression is naturally enhanced in stem and progenitor cells in organs such as blood, skin, intestinal mucosa, endometrium and the like, said stem and progenitor cells which repeatedly regenerate over lifetime, and in lymphocytes which proliferate clonally each time they are exposed to specific antigens. The cell line FERM BP-7498 containing the hTERT which is inserted in between a pair of LoxP sequences is beneficial, because the cell line is not tumorigenic in the case that it is transplanted to an immunodeficiency mouse, and because its doubling time of 48 hours enables large scale culture.

Tamoxifen-induced Cre recombinase herein is a fusion protein which comprises the hormone-binding domain (HBD) in steroid receptors and Cre recombinase. It is preferred that in tamoxifen-induced Cre recombinase, HBD is fused with both the amino terminal and carboxyl terminal of Cre recombinase. Tamoxifen-induced Cre recombinase is inactivated under the condition where HBD and tamoxifen do not bind to each other. Tamoxifen-induced Cre recombinase is activated when tamoxifen binds to HBD.

The HBD in estrogen receptors is defined as a certain region in estrogen receptors which binds to tamoxifen, and it is not limited as long as the region binds to tamoxifen and activates tamoxifen-induced Cre recombinase. For example, when the HBD in estrogen receptors is originated from mouse, the region of amino acid residues 281-599 can be used as the HBD in estrogen receptors. As one used in the present invention, preferable is the HBD in murine estrogen receptor in which the glycine at position 525 is replaced by arginine, because it binds specifically to tamoxifen, but not to 17β-estradiol which exists in a living body (Nucleic Acids Research, 1996, Vol. 24, No. 4, 543-548), and thereby making the control of Cre recombinase easier.

As tamoxifen mentioned above, tamoxifen (available from Sigma, for example) and hydroxy-tamoxifen (available from Sigma, for example) and the like can be used. For removing the hTERT gene which is inserted in LoxP sequences from an immortalized, glucose-sensitive and insulin-secreting hepatic cell line of the present invention, adding 50 nM to 5000 nM of hydroxy-tamoxifen is preferred, and adding 500 nM of hydroxy-tamoxifen is more preferred. When less than 50 nM of hydroxy-tamoxifen is added, the effect of removing the hTERT gene tends to be insufficient. When more than 500 nM of hydroxy-tamoxifen is added, there is a possibility that cytotoxicity might be caused. Adding 1 mM to 100 mM of tamoxifen is preferred, and adding 10 mM of tamoxifen is more preferred. When less than 1 mM of tamoxifen is added, the effect of removing the hTERT gene tends to be insufficient. When more than 100 mM of tamoxifen is added, there is a possibility that cytotoxicity might be caused.

Cre recombinase herein is a known recombinase which specifically recognizes LoxP sequence. Cre recombinase should not be limited as long as it excises the nucleotide sequence flanked by LoxP sequences. According to the present invention, Cre recombinase is used to excise the hTERT gene flanked by LoxP sequences which has been located in the chromosome in a human immortalized hepatic cell line. The cells obtained by excising the hTERT gene flanked by LoxP sequences from the chromosome in an immortal hepatic cells are safe without risks of malignant transformation, and they are suitable for cell transplantation.

Glucose-sensitive promoter is used herein for the expression of insulin gene in a glucose-concentration dependent manner. As a glucose-sensitive promoter, for example, preferably used is the promoter of enzyme genes whose transcription level is known to be controlled correlatively with sugar concentration in glycolytic system and gluconeogenetic system. As a concrete example, LPK promoter (for example, the promoter of rat LPK gene (nucleotide sequence −3193 to +18)), the promoter of phosphoenolpyruvate carboxylase (PEPCK), or the like can be used.

As insulin gene described above, used can be a nucleotide sequence encoding a protein which, for example, promotes the uptake and use of sugar, promotes glycogen synthesis and inhibits gluconeogenesis by specifically binding to insulin receptors and raising the tyrosine-specific enzymatic activity, said insulin receptors being located on the cell-membrane surface of muscular or adipose tissue or liver. Because the hepatic cell line FERM BP-7498 does not have prohormone converting enzymes PC2 and PC1/3 to convert proinsulin into insulin, proinsulin having low bioactivity is secreted when a nucleotide sequence encoding the proinsulin is used. In the present invention, therefore, it is preferred that the nucleotide sequence encoding a recombinant protein in which the C peptide of insulin is replaced by a turn-forming peptide sequence (for example, Gly-Gly-Gly-Pro-Gly-Lys-Arg (SEQ ID NO: 2)), thereby fusing the A and B chains of insulin, is used as an insulin gene. As a nucleotide sequence encoding such recombinant protein, the nucleotide sequence SEQ ID NO: 3 is used.

Any known method can be used as a method of integrating both a sequence encoding tamoxifen-induced Cre recombinase and a sequence encoding insulin into chromosome of cells, said sequence encoding insulin being regulated by a glucose-sensitive promoter. As a method of inducing desired nucleotide sequences to chromosome in cells, used is a method in which virus is not used, such as calcium phosphate transfection or DEAE-dextran method, or a method in which recombinant virus vectors or membrane fusion liposome is used, but not limited thereto.

A medicine for treating diabetes of the present invention comprises the cells obtained by removing the hTERT gene inserted in between a pair of LoxP sequences from the above immortalized hepatic cell line secreting insulin with glucose sensitivity. Together with the cells obtained by removing the hTERT gene, a medicine for treating diabetes of the present invention may contains known and pharmaceutically acceptable excipient or the like.

According to the present invention, the medicine is transplanted into the portal vein as a source for hybrid artificial organ or a source for cell transplantation, for example. The medicine is administered (transplanted) preferably at $1 \times 10^8$ to $1 \times 10^{11}$ cells/individual, more preferably at $1 \times 10^9$ to $1 \times 10^{11}$ cells/individual, and most preferably at $1 \times 10^9$ to $1 \times 10^{10}$ cells/individual.

The present invention is more specifically explained by means of the following Examples. However, it is to be understood that the invention is not limited to only these Examples, without departing from the purpose and the scope of the present invention.

Example 1

In accordance with Dr. Reth's thesis (Nucleic Acids Research, 1996, Vol 24, No. 4), prepared is the expression vector of tamoxifen-induced Cre recombinase in which a nucleotide sequence encoding the amino acid residues 281-599 in murine estrogen receptor in which glycine at position 525 is replaced by arginine (MerG525R), 1050 bp of the cording sequence of Cre recombinase, and a nucleotide sequence encoding MerG525R are fused in this order.

Then, by excising the nucleotide sequence encoding tamoxifen-induced Cre recombinase from the above vector and inserting the resulting nucleotide sequence in the expression vector which comprised CAG promoter and puromycin (Pur) resistance gene, the expression vector (pCAG-Mer-Cre-Mer-Pur) which expressed tamoxifen-induced Cre recombinase in the regulation of CAG promoter was prepared, said CAG promoter comprising the enhancer of cytomegalovirus, the promoter of chicken β-actin and the poly A signal of rabbit β-globin. Because the pCAG-Mer-Cre-Mer-Pur contains Pur resistance gene, it is possible to select the cells to which the vector is introduced.

The cell line FERM BP-7498 was transfected with the above pCAG-MerCre-Mer-Pur by using FuGENE™ 6 transfection reagent (available from Roche Diagnostics), that is,
(1) 40 μl of sterilized water and 10 μl of CAG-MerCre-Mer-Pur (0.4 μg/μl) were added in a 1.5 ml sterilized eppendorf tube, in total 50 μl (Solution 1),
(2) 88 μl of serum-free medium (Dulbecco's modified Eagle medium (DMEM)) and 12 μl of FuGENE are added to a 1.5 ml sterilized eppendorf tube, in total 100 μl (Solution 2),
(3) Solution 1 was added to Solution 2, the solution was mixed by tapping, and then the resulting mixture was allowed to stand for 30 minutes at room temperature,
(4) after culturing the cell line FERM BP-7498 up to 70% confluence in a DMEM supplemented with 10% fetal bovine serum (DMEM+10% FBS), the medium was aspirated from the culture flask to have about 1 ml of the medium left therein, and then the mixture obtained in the above (3) was added, in drops, equally to the surface of the cells, and (5) the mixture was spread over the surface of the cells by slightly tilting the flask, and 2 ml of DMEM+10% FBS was added thereto, followed by culturing the cells over night.

Selection of cells was then performed as follows. The medium was exchanged for a fresh one, followed by one-day cultivation. Then, by exchanging the medium for a fresh DMEM+10% FBS containing 500 nM puromycin, and continuing the cultivation by a ring-cloning method, the cell line TTNT-16-T-3 was established.

To provide the cell line TTNT-16-T-3 with the ability to secrete insulin with glucose sensitivity, the TTNT-16-T-3 was transfected with the plasmid vector pLPK-Alb-SIA-Zeo (an expression vector of the fusion protein in which 72 bp of albumin leader was fused with a recombinant insulin gene (SIA), and which comprised zeosin resistance gene (Zeo) (Nature, 408:483-487, 2000)) by using FuGENE™ 6 transfection reagent as mentioned above, said albumin leader promoting the insulin secretion in the regulation of L-type pyruvate kinase promoter (nucleotide sequence of −3193 to +18).

Selection of cells was then performed as follows. The medium was exchanged for a fresh one, followed by one-day cultivation. Then, by exchanging the medium for a flesh DMEM+10% FBS containing 100 μg/ml zeosin, and continuing the cultivation by a ring-cloning method, an immortalized hepatic cell line secreting insulin with glucose sensitivity was established. The cell line was deposited with International Patent Organism Depositary, National Institute of Advanced Industrial Science and Technology, AIST Tsukuba Central 6, 1-1, Higashi 1-Chome Tsukuba-shi, Ibaraki-ken (accession number FERM BP-8127).

Test Example 1

Expression of LPK Gene in Response to the Change of Glucose Concentration

The cell line FERM BP-8127 ($1 \times 10^6$ cells) was inoculated into five 10 cm petri dishes, and cultivated up to 80% confluence by using Dulbecco's Modified Eagle Medium (DMEM) containing 1 μg/ml zeosin and 100 mg/dl glucose. The medium was then exchanged for DMEM containing 500 nM tamoxifen (available from Sigma), 1 μg/ml zeosin and 100 mg/dl glucose, followed by one-week cultivation. Next, the medium was exchanged for DMEM supplemented with 400 mg/dl glucose, 1 μg/ml zeosin and 500 nM tamoxifen, followed by 24-hour cultivation. As a result, $1 \times 10^7$ cells per petri dish were obtained.

The cells were collected after the cultivation, and then total RNA was extracted from the cells. The obtained RNA was separated by electrophoresis, and then Northern blotting was performed by using a probe against LPK. As control cells, used were the cells which were inoculated and cultivated under the same condition as mentioned above except that glucose was not added. In Northern blotting, 28S rRNA was used as an internal control, and detected by ethidium bromide staining.

A result of Northern blotting is shown in FIG. 1. In FIG. 1, lane 1 shows a result of control cells, and lane 2 shows a result of glucose-sensitive hepatic cells to which glucose was added. By adding glucose, the expression of LPK gene was enhanced in the cells in which the TERT gene were removed from FERM BP-8127 by addition of tamoxifen, whereas an enhanced expression of LPK gene was not observed in control cells.

Test Example 2

Expression of Insulin in Response to the Change of Glucose Concentration

The cell line FERM BP-8127 ($1 \times 10^6$ cells) was inoculated into five 10 cm petri dishes, and cultivated up to 80% confluence by using Dulbecco's modified Eagle medium (DMEM) containing 1 μg/ml zeosin and 100 mg/dl glucose. The medium was then exchanged for DMEM supplemented with 500 nM tamoxifen (available from Sigma), 1 μg/ml zeosin and 100 mg/dl glucose, followed by one-week cultivation. The medium was then exchanged for DMEM supplemented with 400 mg/dl glucose, 1 μg/ml zeosine and 500 nM tamoxifen, followed by further 24-hour cultivation. As a result, $1 \times 10^7$ cells per petri dish were obtained.

After the cultivation, the expression of insulin in the cells was investigated by immunostaining using anti-insulin antibody. As control cells, used were the cells obtained by carrying out inoculation, cultivation and TERT-gene removal under the same condition as mentioned above except that glucose was not added.

Figure 2:
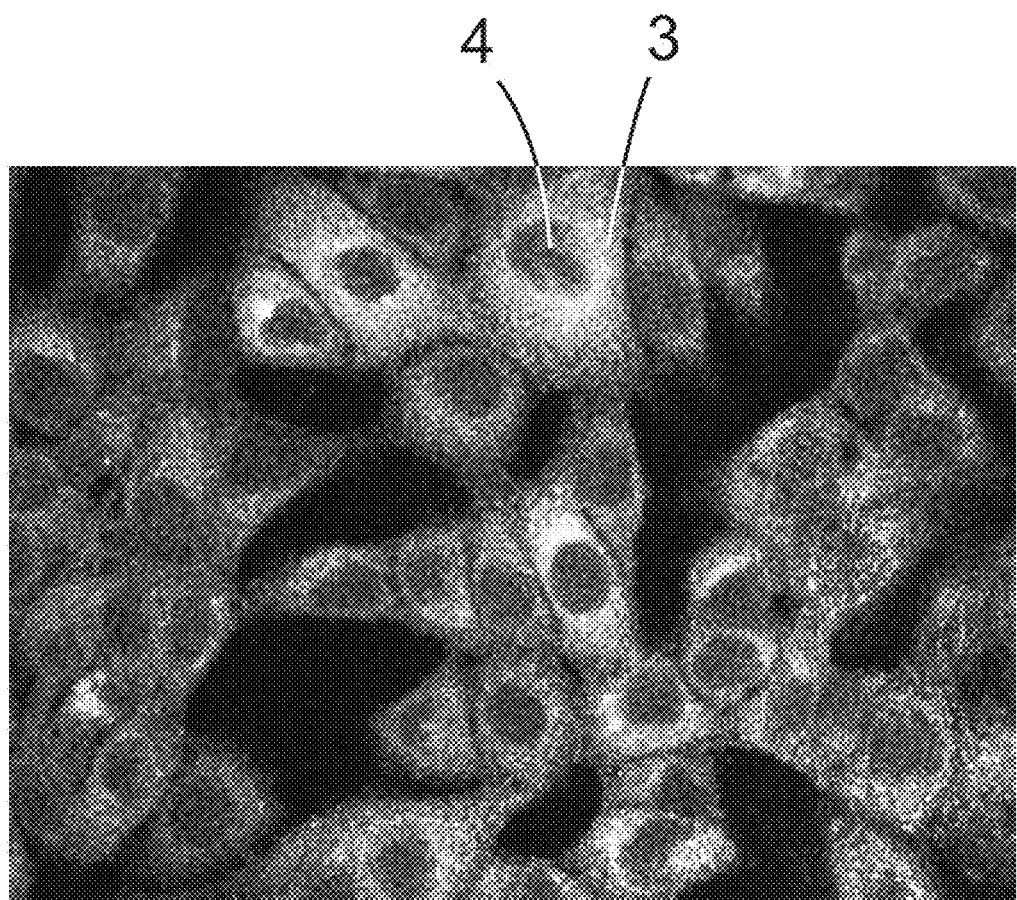
FIG. 2 is a figure showing a result obtained by adding glucose to hepatic cells which secrete insulin with glucose sensitivity, and detecting the insulin expression in a glucose dependent manner by immunostaining.

As a result, it was confirmed that by increasing glucose concentration, the cells which were obtained by removing TERT gene from FERM BP-8127 expressed a high concentration of insulin (FIG. 2), whereas insulin was not detected in the control cells to which glucose was not added.

Test Example 3

Effect of Glucose-Sensitive and Insulin-Secreting Hepatocyte Transplantation into the Subrenal Capsule on Diabetic Mouse The cell line FERM BP-8127 ($1 \times 10^6$ cells) was inoculated into five 10 cm petri dishes, and cultivated up to 80% confluence by using DMEM containing 1 μg/ml zeosin and 100 mg/dl glucose. The medium was then exchanged for DMEM containing 500 nM tamoxifen (available from Sigma), 1 μg/ml zeosin and 100 mg/dl glucose, followed by a week's cultivation. The medium was then exchanged for DMEM containing 400 mg/dl glucose, 1 μg/ml zeosine and 500 nM tamoxifen, followed by further 24-hour cultivation. As a result, 1×10$^7$ cells per petri dish were obtained.

Diabetic mice were prepared by administering to mice drug, streptozocin (210 mg/kg). Mice were decided as to be diabetic, when the blood sugar level became more than 400 mg/dl. After making an incision in the abdomen, said cells (1×10$^7$ cells) were transplanted into the subrenal capsule (n=5). The blood sugar level was measured after the cell transplantation, and then the effect of the cell transplantation was judged. In this test, a diabetic mouse which was not subjected to cell transplantation was used as control A.

Figure 3:
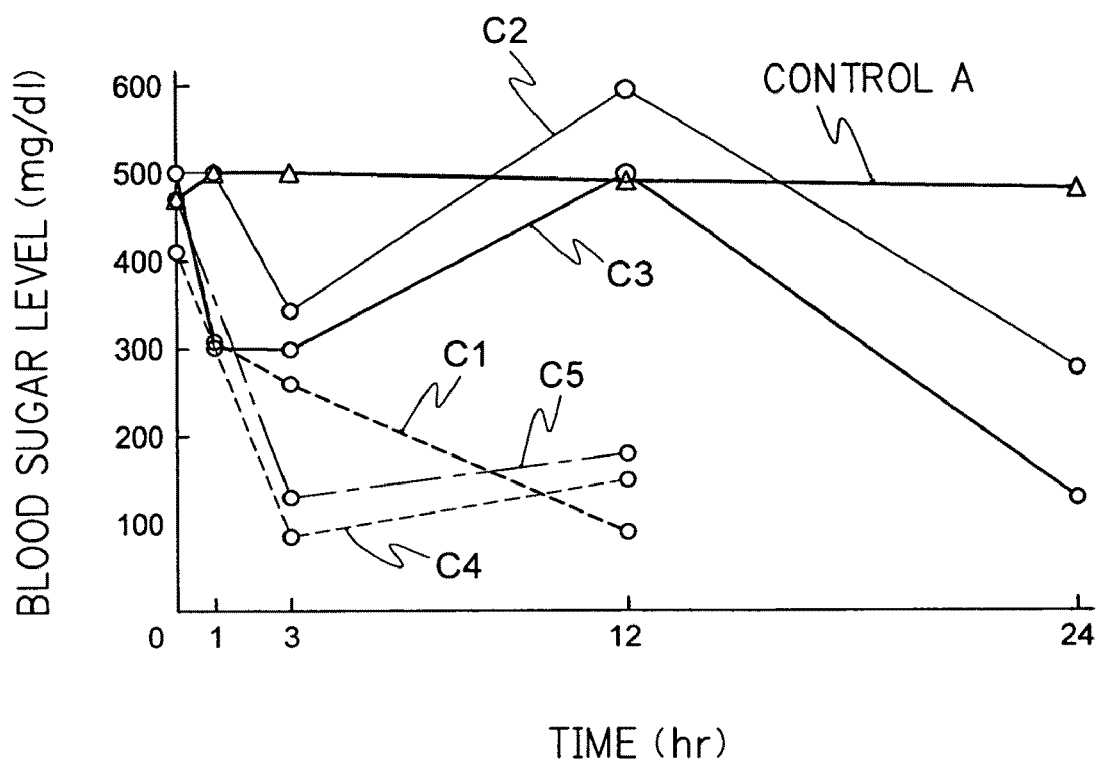
FIG. 3 is a graph showing the blood sugar level in diabetic mice to which cell transplantation into the subrenal capsule was applied.

A result of the cell transplantation is shown in FIG. 3. In FIG. 3, each of C1-C5 denotes a diabetic mouse which was subjected to cell transplantation into the subrenal capsule. In each mouse subjected to cell transplantation into the subrenal capsule, it was shown that the blood sugar level was decreased. In control A which was not subjected to cell transplantation into the subrenal capsule, it was shown that the blood sugar level was constantly more than 400 mg/dl. The result shows that the transplanted cells secrete insulin in response to the blood sugar level.

Test Example 4

Effect of Glucose-Sensitive and Insulin-Secreting Hepatocyte Transplantation in Abdominal Cavity on Diabetic Mouse The cell line FERM BP-8127 (1×10$^6$ cells) was inoculated into nine 10 cm petri dishes, and cultivated up to 80% confluence by using DMEM containing 1 μg/ml zeosin and 100 mg/dl glucose. The medium was then exchanged for DMEM containing 500 nM tamoxifen (available from Sigma), 1 μg/ml zeosin and 100 mg/dl glucose, followed by a week's cultivation. The medium was then exchanged for DMEM containing 400 mg/dl glucose, 1 μg/ml zeosine and 500 nM tamoxifen, followed by further 24-hour cultivation. As a result, 1×10$^7$ cells per petri dish were obtained.

Diabetic mice were prepared by administering to mice drug, streptozocin (210 mg/kg). Mice were decided as to be diabetic, when the blood sugar level became more than 400 mg/dl. After making an incision in the abdomen, said cells (3×10$^7$ cells) were transplanted in the abdominal cavity (n=2). The blood sugar level was measured after the cell transplantation, and then the effect of the cell transplantation was judged. As in TEST EXAMPLE 3, a diabetic mouse which was not subjected to cell transplantation was used as control A in this test. In addition, a normal mouse which was subjected to transplantation in the abdominal cavity by using 3×10$^7$ cells was used as control B.

Figure 4:
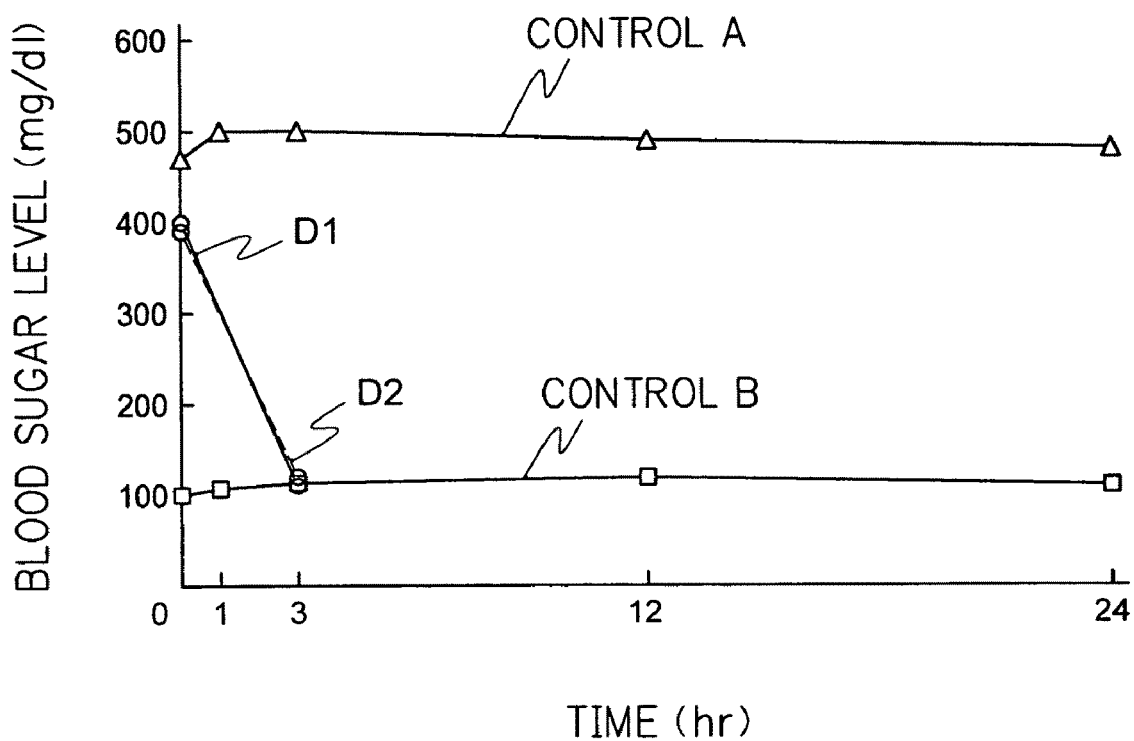
FIG. 4 is a graph showing the blood sugar level in diabetic mice to which cell transplantation in the abdominal cavity was applied.

A result of the transplantation is shown in FIG. 4. In FIG. 4, each of D1 and D2 denotes a diabetic mouse which was subjected to cell transplantation in the abdominal cavity. In each mouse subjected to cell transplantation in the abdominal cavity, it was shown that the blood sugar level was decreased. In control A which was not subjected to cell transplantation in the abdominal cavity, it was shown that the blood sugar level was constantly more than 400 mg/dl, whereas the blood sugar level in control B did not decrease. The result shows that the transplanted cells secrete insulin in response to the blood sugar level.

INDUSTRIAL APPLICABILITY

According to the present invention, provided was an immortalized hepatocyte cell line secreting insulin with glucose sensitivity, said cell line which can express insulin in a glucose-concentration dependent manner, and enables the easy obtainment of the number of cells which meets the demand. Extremely useful for curing diabetes are cells which are obtained by removing the hTERT gene inserted in between a pair of LoxP sequences from the cell line, because these cells are substituted for β cells in human mature pancreatic islets; it is not easy to handle said β cells, and β cells are in short supply. An immortalized hepatocyte cell line secreting insulin with glucose sensitivity, FERM BP-8127, of the present invention is an extremely superior cell line in particular, because the cell line is not tumorigenic even in the case that the cell line is transplanted to an immunodeficiency mouse, as well as maintaining hepatocyte-specific gene expressions.

In addition, by using the cells of the present invention as a material, it is possible to develop a bio-artificial pancreas such as a hybrid artificial pancreas in which diffusion-chamber type, micro-capsule shaped, or hollow-fiber type module (device) is combined with separated and cultured cells.

The invention claimed is:

1. A hepatocyte cell line that secretes insulin in response to glucose, which is obtained by integrating both a nucleotide sequence encoding a tamoxifen-induced Cre recombinase comprising a hormone-binding domain that is an estrogen receptor, and a nucleotide sequence encoding insulin regulated by a glucose-sensitive promoter into a chromosome in an immortalized hepatic cell of the human immortalized hepatic cell line FERM BP-7498, which human immortalized hepatic cell line has an hTERT gene inserted between a pair of LoxP sequences, and then removing the hTERT gene inserted between the pair of LoxP sequences.

2. The hepatocyte cell line that secretes insulin in response to glucose sensitivity of claim 1, wherein the estrogen receptor is a murine estrogen receptor in which the glycine at position 525 is replaced by arginine, with the hormone-binding domain being fused with the Cre recombinase.

3. A medicine for treating diabetes, which comprises cells obtained by removing the hTERT gene inserted between a pair of LoxP sequences from an immortalized hepatic cell line that secretes insulin in response to glucose which is obtained by integrating both a nucleotide sequence encoding tamoxifen-induced CRE recombinase comprising a hormone-binding domain that is an estrogen receptor, and a nucleotide sequence encoding insulin regulated by a glucose sensitive promoter into a chromosome in an immortalized hepatic cell of the human immortalized hepatic cell line FERM BP-7498.

4. The medicine according to claim 3, wherein the tamoxifen-induced Cre recombinase comprises a hormone-binding domain of a murine estrogen receptor in which the glycine at position 525 is replaced by arginine, with the hormone-binding domain being fused with the Cre recombinase.

* * * * *